US00PP20919P2

(12) United States Plant Patent
Brown

(10) Patent No.: US PP20,919 P2
(45) Date of Patent: Apr. 6, 2010

(54) ***MANDEVILLA* PLANT NAMED 'VOG 053'**

(50) Latin Name: *Mandeville hybrida*
Varietal Denomination: VOG 053

(75) Inventor: Graham Noel Brown, Pennant Hills (AU)

(73) Assignees: Floraquest Pty. Ltd., Pennant Hills, NSW (AU); Protected Plants Promotions Australia Pty. Ltd., Macquarie Fields, NSW (AU)

( * ) Notice: Subject to any disclaimer, the term of this patent is extended or adjusted under 35 U.S.C. 154(b) by 0 days.

(21) Appl. No.: 12/291,555

(22) Filed: Nov. 12, 2008

(51) Int. Cl.
*A01H 5/00* (2006.01)

(52) U.S. Cl. ..... Plt./232

(58) Field of Classification Search ..... Plt./232
See application file for complete search history.

*Primary Examiner*—Annette H Para
(74) *Attorney, Agent, or Firm*—C. A. Whealy

(57) ABSTRACT

A new and distinct cultivar of *Mandevilla* plant named 'VOG 053', characterized by its compact, upright and mounded plant habit; strong stems; freely branching habit; freely flowering habit; and dark red-colored flowers.

1 Drawing Sheet

Botanical designation: *Mandevilla hybrida.*
Cultivar denomination: 'VOG 053'.

BACKGROUND OF THE INVENTION

The present invention relates to a new and distinct cultivar of *Mandevilla* plant, botanically known as *Mandevilla hybrida* and hereinafter referred to by the name 'VOG 053'.

The new *Mandevilla* plant is a product of a planned breeding program conducted by the Inventor in New South Wales, Australia. The objective of the breeding program is to create new compact shrub-type *Mandevilla* cultivars with strong stems and numerous attractive flowers.

The new *Mandevilla* plant originated from a cross-pollination made by the Inventor in Pennant Hills, New South Wales, Australia in December, 2003, of a proprietary selection of *Mandevilla hybrida* identified as code number X02.5, not patented, as the female, or seed parent with *Mandevilla hybrida* 'Sunmandecrim', disclosed in U.S. Plant Pat. No. 15,539, as the male, or pollen, parent. The new *Mandevilla* was discovered and selected by the Inventor as a single flowering plant from within the progeny of the stated cross-pollination in a controlled greenhouse environment in Macquarie Fields, New South Wales, Australia in November, 2005.

Asexual reproduction of the new *Mandevilla* plant by cuttings in Macquarie Fields, New South Wales, Australia, since December, 2005, has shown that the unique features of this new *Mandevilla* plant are stable and reproduced true to type in successive generations.

SUMMARY OF THE INVENTION

Plants of the new *Mandevilla* have not been observed under all possible environmental conditions. The phenotype may vary somewhat with variations in environment such as temperature and light intensity without, however, any variance in genotype.

The following traits have been repeatedly observed and are determined to be the unique characteristics of 'VOG 053'. These characteristics in combination distinguish 'VOG 053' as a new and distinct cultivar:

1. Compact, upright and mounded plant habit.
2. Strong stems.
3. Freely branching habit.

4. Freely flowering habit.
5. Dark red-colored flowers.

Plants of the new *Mandevilla* can be compared to plants of the female parent selection. Plants of the new *Mandevilla* differ from plants of the female parent selection in the following characteristics:

1. Plants of the new *Mandevilla* have smaller flowers than plants of the female parent selection.
2. Plants of the new *Mandevilla* and the female parent selection differ in flower color as plants of the female parent selection have lighter-colored flowers.

Plants of the new *Mandevilla* can be compared to plants of the male parent, 'Sunmandecrim'. Plants of the new *Mandevilla* differ from plants of 'Sunmandecrim' in the following characteristics:

1. Plants of the new *Mandevilla* are more compact than plants of 'Sunmandecrim'.
2. Plants of the new *Mandevilla* and 'Sunmandecrim' differ in flower color as plants of 'Sunmandecrim' have darker red-colored flowers.

Plants of the new *Mandevilla* can also be compared to plants of *Mandevilla splendens* 'Audrey', disclosed in U.S. Plant patent application Ser. No. 12/291,395. Plants of the new *Mandevilla* differ from plants of 'Audrey' primarily in flower color as plants of 'Audrey' have darker red-colored flowers.

BRIEF DESCRIPTION OF THE PHOTOGRAPHS

The accompanying colored photographs illustrate the overall appearance of the new *Mandevilla* plant, showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph at the bottom of the sheet comprises a top perspective view of a typical flowering plant of 'VOG 053' grown in a container.

The photograph at the top of the sheet is a close-up view of typical flowers, flower buds and leaves of 'VOG 053'.

DETAILED BOTANICAL DESCRIPTION

The aforementioned photographs and following observations, measurements and values describe plants grown in Bonsall, Calif., under commercial practice during the late summer and early autumn in an outdoor nursery. During the production of the plants, day temperatures ranged from 20° C. to 32° C. and night temperatures ranged from 7° C. to 21° C. Plants were pinched one time and had been growing for 18 months when the description and photographs were taken. In the following description, color references are made to The Royal Horticultural Society Colour Chart, 2001 Edition, except where general terms of ordinary dictionary significance are used.

Botanical classification: *Mandevilla hybrida* 'VOG 053'.

Parentage:

*Female, or seed, parent*.—Proprietary selection of *Mandevilla hybrida* identified as code number X02.5, not patented.

*Male, or pollen, parent*.—*Mandevilla hybrida* 'Sunmandecrim', disclosed in U.S. Plant Pat. No. 15,539.

Propagation:

*Type*.—By cuttings.

*Time to produce a rooted young plant*.—About one month.

*Root description*.—Fleshy, thick; white in color.

*Rooting habit*.—Moderate branching; moderately dense.

Plant description:

*Plant habit*.—Compact, upright and mounding.

*Growth habit*.—Vigorous.

*Plant height*.—About 50 cm.

*Plant diameter*.—About 68 cm.

*Lateral branch description*.—Branching habit: Freely branching with about ten to twelve primary lateral branches per plant. Length: About 52 cm. Diameter: About 8 mm to 11 mm. Internode length: About 3 cm. Strength: Strong. Texture: Smooth, glabrous. Color: Close to 146B.

Foliage description:

*Arrangement*.—Opposite, simple.

*Length*.—About 6.2 cm.

*Width*.—About 4.4 cm.

*Shape*.—Elliptical.

*Apex*.—Acuminate.

*Base*.—Obtuse.

*Margin*.—Entire.

*Texture, upper and lower surfaces*.—Smooth, glabrous; leathery.

*Venation pattern*.—Pinnate, arcuate.

*Color*.—Developing leaves, upper surface: Close to 146A. Developing leaves, lower surface: Close to 146B. Fully expanded leaves, upper surface: Close to 147A; venation, close to 139A. Fully expanded leaves, lower surface: Close to 147B; venation, close to 146C.

*Petioles*.—Length: About 1.4 cm. Diameter: About 2 mm. Texture, upper and lower surfaces: Smooth, glabrous. Color, upper surface: Close to 146C. Color, lower surface: Close to 146D.

Flower description:

*Flower type and habit*.—Salverform flowers arranged in loose and open racemes. Flowers face upright or outwardly. Freely flowering habit, about 24 to 27 open flowers and flower buds per lateral branch.

*Natural flowering season*.—Long flowering period; plants flower from year-round in the greenhouse and from spring to late autumn in California; flowering continuous during this period. Plants initiate flower development about six weeks after planting.

*Flower longevity on the plant*.—About four to five days; flowers not persistent.

*Fragrance*.—Faint; sweet.

*Inflorescence height*.—About 10 cm to 10.5 cm.

*Inflorescence diameter*.—About 7.5 cm.

*Flowers*.—Appearance: Flared trumpet, corolla fused, five-parted; petals imbricate; flowers roughly star-shaped. Diameter: About 6.4 cm. Depth (length): About 6 cm. Throat diameter: About 1.7 cm. Tube length: About 6 cm. Tube diameter, mid-section: About 1.5 cm. Tube diameter, base: About 4 mm.

*Flower buds*.—Height: About 6.8 cm. Diameter: About 1.3 cm. Shape: Elongated oblong. Color: Close to 60C.

*Corolla*.—Arrangement/appearance: Single whorl of five petals, fused into flared trumpet; petals imbricate. Petal lobe length: About 3.1 cm. Petal lobe width: About 2.5 cm. Petal shape: Roughly elliptical. Petal apex: Acuminate, reflexing. Petal margin: Entire. Petal texture, upper and lower surfaces: Smooth, glabrous; velvety. Color: Petal lobe, when opening, upper surface: Close to N34A. Petal lobe, when opening, lower surface: Close to 60B. Petal lobe, fully opened, upper surface: Close to 53A; towards the base, close to 46A; color does not fade with development. Petal lobe, fully opened, lower surface: Close to 59B to 59C; color does not fade with development. Tube: Towards the apex, close to 60B; mid-section, close to 145C; towards the base, close to 145B. Throat: Close to 26A.

*Sepals*.—Arrangement/appearance: Five per flower fused in a single whorl. Length: About 7 mm. Width: About 2 mm. Shape: Lanceolate. Apex: Acute. Margin: Entire. Texture, upper and lower surfaces: Smooth, glabrous. Color, upper surface: Close to 145C. Color, lower surface: Close to 145B.

*Peduncles*.—Length: About 3.7 cm. Diameter: About 2 mm. Texture: Smooth, glabrous. Strength: Flexible, but strong. Color: Close to 144A.

*Pedicels*.—Length: About 2.4 cm. Diameter: About 2.5 mm. Texture: Smooth, glabrous. Strength: Flexible, but strong. Color: Close to 146B.

*Reproductive organs*.—Stamens: Quantity per flower: Typically five. Filament length: About 2 mm. Filament color: Close to 145D. Anther shape: Lanceolate. Anther size: About 2 mm by 9 mm. Anther color: Close to 11C. Pollen amount: Scarce. Pollen color: Close to 11D. Pistils: Quantity per flower: Typically one. Pistil length: About 2.6 cm. Stigma shape: Rounded. Stigma color: Close to 146D. Style length: About 2.2 cm. Style color: Close to 145C. Ovary color: Close to 144A.

*Seed/fruit*.—Seed and fruit production has not been observed.

Disease/pest resistance: Plants of the new *Mandevilla* have not been noted to be resistant to pathogens and pests common to *Mandevilla*.

Temperature tolerance: Plants of the new *Mandevilla* have been observed to tolerate temperatures from about 4° C. to about 35° C.

It is claimed:

1. A new and distinct *Mandevilla* plant named 'VOG 053' as illustrated and described.

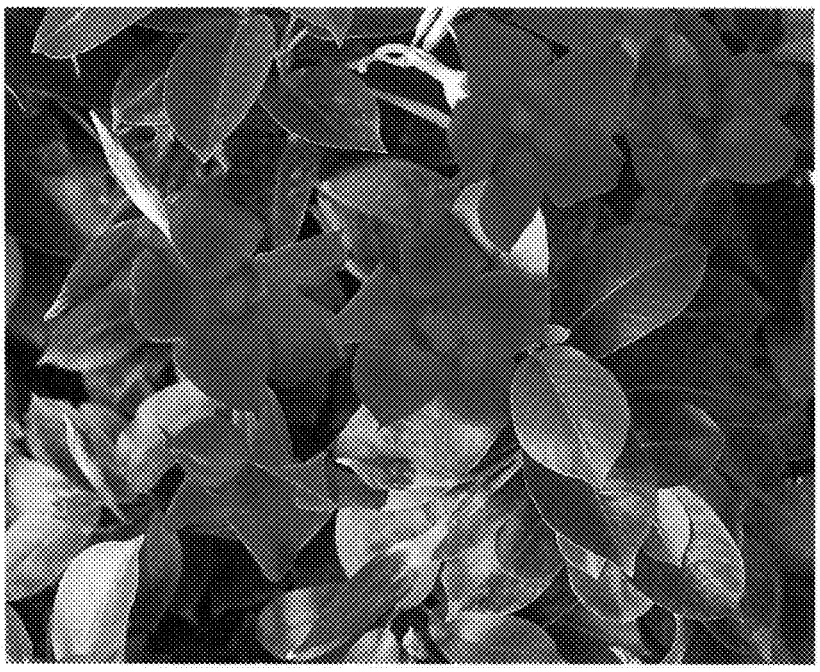
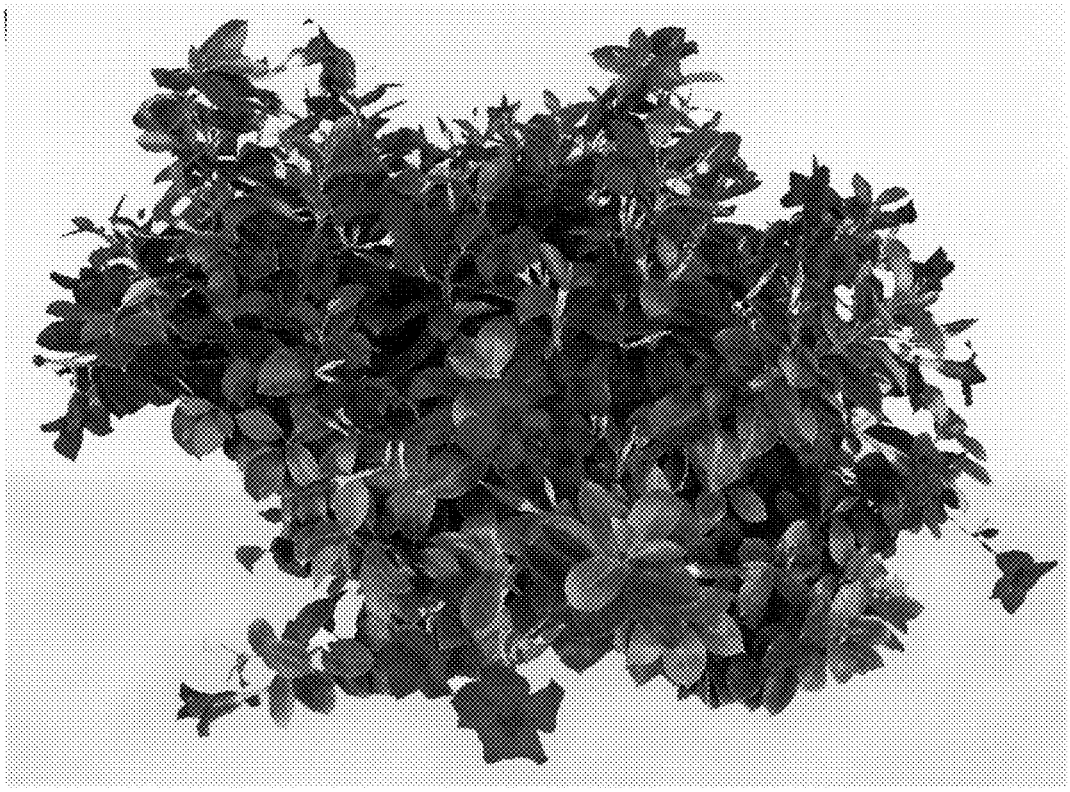

* * * * *